US009675710B2

(12) United States Patent
Rodriguez Gascôn et al.

(10) Patent No.: US 9,675,710 B2
(45) Date of Patent: Jun. 13, 2017

(54) LIPID NANOPARTICLES FOR GENE THERAPY

(75) Inventors: Alicia Rodriguez Gascôn, Leioa-Vizcaya (ES); Maria Angeles Solinís Aspíazu, Leioa-Vizcaya (ES); Ana Del Pozo Rodriguez, Leioa-Vizcaya (ES); Diego Delgado San Vicente, Leioa-Vizcaya (ES); José Luis Pedraz Muñoz, Leioa-Vizcaya (ES)

(73) Assignee: UNIVERSIDAD DEL PAIS VASCO, Leioa-Vizcaya (ES)

( * ) Notice: Subject to any disclaimer, the term of this patent is extended or adjusted under 35 U.S.C. 154(b) by 119 days.

(21) Appl. No.: 13/386,611

(22) PCT Filed: Jul. 27, 2010

(86) PCT No.: PCT/ES2010/070519
§ 371 (c)(1),
(2), (4) Date: Apr. 3, 2012

(87) PCT Pub. No.: WO2011/015701
PCT Pub. Date: Feb. 10, 2011

(65) Prior Publication Data
US 2012/0183589 A1  Jul. 19, 2012

(30) Foreign Application Priority Data
Jul. 28, 2009 (ES) .................................. 200901664

(51) Int. Cl.
| *A61K 8/02* | (2006.01) |
| *A61K 48/00* | (2006.01) |
| *A61K 38/02* | (2006.01) |
| *A61K 31/7088* | (2006.01) |
| *A61K 31/7105* | (2006.01) |
| *A61K 31/711* | (2006.01) |
| *A61K 9/14* | (2006.01) |
| *A61K 31/715* | (2006.01) |
| *A61K 9/00* | (2006.01) |
| *A61K 9/51* | (2006.01) |
| *A61K 38/01* | (2006.01) |

(52) U.S. Cl.
CPC ........ *A61K 48/0025* (2013.01); *A61K 9/0019* (2013.01); *A61K 9/5123* (2013.01); *A61K 9/5161* (2013.01); *A61K 38/014* (2013.01)

(58) Field of Classification Search
None
See application file for complete search history.

(56) References Cited

U.S. PATENT DOCUMENTS

| 2006/0083781 A1 | 4/2006 | Shastri et al. |
| 2006/0189554 A1 | 8/2006 | Mumper et al. |
| 2007/0020336 A1 | 1/2007 | Loftsson et al. |
| 2007/0237826 A1 * | 10/2007 | Rao ....................... A61K 9/0019 424/489 |
| 2008/0160096 A1 | 7/2008 | Berbely et al. |
| 2008/0206341 A1 | 8/2008 | Gasco |
| 2008/0213350 A1 | 9/2008 | Ko et al. |
| 2012/0183589 A1 | 7/2012 | Rodriguez Gascon et al. |

FOREIGN PATENT DOCUMENTS

| EP | 2460516 | 6/2012 |
| ES | 2351756 | 2/2011 |
| WO | WO-00/06120 | 2/2000 |
| WO | WO02/076441 | * 3/2002 |
| WO | WO-02/076441 | 10/2002 |
| WO | WO-2004/082660 | 9/2004 |
| WO | WO-2004/096140 | 11/2004 |
| WO | WO2005/041933 | * 5/2005 |
| WO | WO-2005/041933 | 5/2005 |
| WO | WO-2005/120469 | 12/2005 |
| WO | WO-2006/087752 | 8/2006 |
| WO | WO-2007/135164 | 11/2007 |
| WO | WO-2010/008582 | 1/2010 |

OTHER PUBLICATIONS

Wong et al. "Development of Solid Lipid Nanoparticles Containing Ionically Complexed Chemotherapeutic Drugs and Chemosensitizers", Journal of Pharmaceutical Sciences, 93(8), 2004, pp. 1993-2008.*
Rudolph et al., "Application of Novel Solid Lipid Nanoparticle (SLN)-Gene Vector Formulations Based on a Dimeric HIV-1 TAT-Peptide in Vitro and in Vivo", Pharmaceutical Research, 21(9), 2004, pp. 1662-1669.*
Brake et al., "Identification of an Arg-Gly-Asp (RGD) Cell Adhesion Site in Human Immundodeficiency Virus Type 1 Transactivation Protein, tat", The Journal of Cell Biology, 111, 1990, pp. 1275-1281.*
"PCT International Search Report for PCT/ES2010/070519", Nov. 30, 2010 , 3 pages.
Del Pozo-Rodriguez, A. et al., "A Proline-Rich Peptide Improves Cell Transfection of Solid Lipid Nanoparticle-Based Non-Viral Vectors", *Journal of Controlled Release* vol. 133 2009 , 52-59.
Del Pozo-Rodríguez, A. et al., "Solid Lipid Nanoparticles: Formulation Factors Affecting Cell Transfection Capacity", *International Journal of Pharmaceutics* vol. 339 2007 , 261-268.

(Continued)

*Primary Examiner* — Melissa Javier
(74) *Attorney, Agent, or Firm* — Lucas & Mercanti, LLP

(57) ABSTRACT

The present invention relates to a lipid nanoparticle system comprising a lipid component, a cationic surfactant, a non-ionic surfactant, a polysaccharide and, optionally, a positively charged peptide, useful for the release of pharmacologically active molecules, and especially for transfecting genetic material into cells and/or tissues. It also relates to methods for obtaining nanoparticles, to pharmaceutical compositions comprising it, as well as to the use thereof in gene therapy.

10 Claims, 7 Drawing Sheets

(56) References Cited

OTHER PUBLICATIONS

Delgado, Diego et al., "Understanding the mechanism of protamine in solid lipid nanoparticle-based lipofection: The importance of the entry pathway", *European Journal of Pharmaceutics and Biopharmaceutics* 79 2011, 495-502.

International Search Report for WO2012085318, mailed Apr. 16, 2012, 4 pages.

Apaolaza, P. S. et al., "Solid lipid nanoparticle-based vectors intended for the treatment of X-linked juvenile retinoschisis by gene therapy: In vivo approaches in Rs1h-deficient mouse model", *Journal of Controlled Release* 217:273-283 dated Sep. 21, 2015, 11 pages.

De La Fuente, et al., "Chitosan-based nanostructures: A delivery platform for ocular therapeutics," *Advanced Drug Delivery Reviews* 62:100-117, published online on Dec. 2009.

Del Pozo-Rodriguez, et al., "Solid lipid nanoparticles for retinal gene therapy: transfection and intracellular trafficking in RPE cells", *International Journal of Pharmaceutics*, Apr. 22, 2008, vol. 360, No. 1-2, pp. 177-183.

Fattal, Elias et al., "Nanotechnologies and controlled release systems for the delivery of antisense oligonucleotides and small interfering RNA", *British Journal of Pharmacology* vol. 157 2009, 179-194.

Khar, R.K. et al., "Nano-vectors for the ocular delivery of nucleic acid-based therapeutics", *Indian J. Pharm. Sci.* Vo. 72 Issue 6 2010, 675-688.

Kingston, R.E., "Current Protocols in Molecular Biology", 2003, 190 pages.

Maruyama, Kazuo et al., "Novel receptor-mediated gene delivery system comprising plasmid/protamine/sugar-containing polyanion ternary complex", *Biomaterials*, vol. 25, No. 16, (2004) pp. 3267-3273.

Min, Seok H. et al., "Prolonged Recovery of Retinal Structure/Function after Gene Therapy in an Rs1h-eficient Mouse Model of X-Linked Juvenile Retinoschisis", *Molecular Therapy* vol. 12, No. 4 Oct. 2005, 644-651.

Spiga, Maria-Grazia et al., "Development of a Gene Therapy Virus with a Glucocorticoid-Inducible MMP1 for the Treatment of Steroid Glaucoma", *Investigative Ophthalmology & Visual Science*, vol. 51, No. 6 Jun. 2010, 3029-3041.

Stegmann, Toon et al., "Gene transfer mediated by cationic lipids: lack of a correlation between lipid mixing and transfection", *Biochimica et Biophysica Acta*, 1325:71-79 dated Sep. 1997.

* cited by examiner

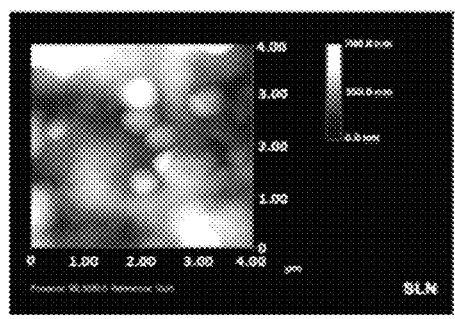
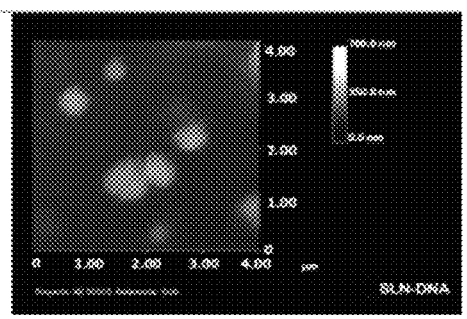
Figure 1A   Figure 1B
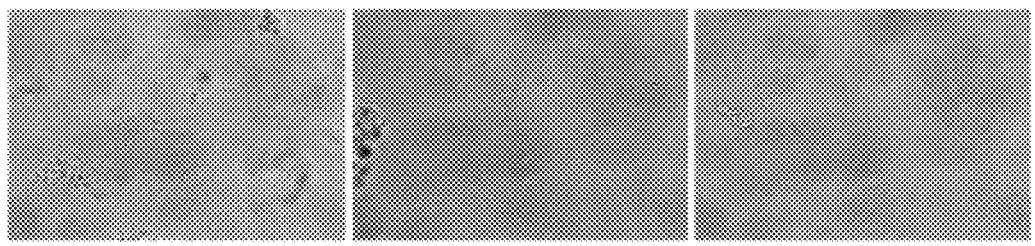
Figure 2

LIPID NANOPARTICLES FOR GENE THERAPY

CROSS-REFERENCE TO RELATED APPLICATIONS

This application is the national stage entry of PCT/ES2010/070519, filed on Jul. 17, 2010, which claims priority to Spain Patent application number P200901664, filed on Jul. 28, 2009, both of which are incorporated herein by reference in their entireties.

FIELD OF THE INVENTION

The present invention relates to a lipid nanoparticle system useful for the release of pharmacologically active molecules, and especially for transfecting genetic material into cells and/or tissues, as well as methods for obtaining it and pharmaceutical compositions comprising it.

BACKGROUND

In the last few decades a wide range of reagents and techniques for transferring genetic material into cells for the purpose of modulating gene expression both in vitro and in vivo have been developed. Most efforts in this field are focused on the search for systems with greater efficiency and on new applications. These efforts have allowed obtaining sophisticated reagents and useful technologies for producing proteins with clinical and research applications, for adding genetic markers to a cell line and for modifying the protein expression of a cell to evaluate the effect of a gene (overexpression or reduction of expression).

Gene therapy is a very promising therapeutic tool for treating a wide range of hereditary or acquired diseases. Recent advances in molecular biology and knowledge of the human genome have allowed making valuable information on cell processes and the pathogenesis of many diseases available. In the last few years many genes involved in pathological processes have been identified; furthermore expression systems of those genes are being widely investigated so they can be used for therapeutic purposes. However, the development of new therapeutic strategies using this biological material depends on the capacity for manipulating the expression of these genes in suitable cells.

The number of diseases which can potentially be treated by means of gene therapy is very large, and they include among others, autosomal recessive diseases due to the defect of a single gene (cystic fibrosis, hemophilia, Fabry disease, etc.), autosomal dominant diseases, some cancers, HIV and other infectious diseases, inflammatory diseases, etc.

Gene therapy consists of introducing genetic material (DNA, RNA or antisense sequences) into target cells for the purpose of modulating the expression of specific proteins which are altered, thus reversing the biological disorder causing the alteration thereof. Naked genes can be locally administered into specific organs such as the muscle or liver by physical means such as electroporation or hydrodynamic injection. However, these methods are not useful for systemic administration or are nonviable from the viewpoint of marketing them as drugs. To develop a gene therapy product, not only the disease to be treated and the therapeutic gene to be administered must be taken into account, rather what is very important is the administration system of that gene. It is necessary that the administration system is capable of protecting the genetic material against enzymatic degradation and that it facilitates the cell uptake and subsequent release in the cell cytoplasm. Furthermore, it must allow controlling the localization of the gene in the organism as well as the duration of the gene expression. The gene administration systems can be classified as viral or non-viral vectors. The viral vectors are the most effective, but have large immunogenicity and oncogenicity problems. Another drawback is that they can only include small-sized genes.

Due to the drawbacks of these viral transfection systems, there is a serious need for developing non-viral transfection systems with a suitable transfection efficacy entailing an alternative better than using the viral vectors. The non-viral vectors are in fact much safer, their production is simpler and cheaper and do not have limitation in terms of the size of the genetic material to be included. In this sense, the nanoparticle-based systems have shown to be useful as transfection systems. Thus, application US2008/0160096 describes the production of nanoparticles based on complexing a polycation with one or more nucleic acids, said complex being coated with a polyanion. Application WO2007/135164 in turn relates to the preparation of nanoparticles based on chitosan and hyaluronan for associating genetic material, its particular use for transfecting ocular tissue being demonstrated.

In the literature there are also several documents which describe obtaining and using lipid nanoparticles as vectors for transporting genetic material to cells (WO2005/120469, WO2006/087752, WO2004/096140 and US2008/0213350). The document of Del Pozo-Rodriguez et al. (*J. Control. Rel.*, 2009, 133, 52-59) particularly refers to a lipid nanoparticle system further incorporating ionic surfactants, where said nanoparticles are contacted with a complex made up of a plasmid and a peptide for coating the latter. Lipid nanoparticles also incorporating a peptide therein are described in WO00/06120. Application US2006/0189554 in turn describes a vaccine incorporating a lipid nanoparticle system on which surface there is deposited an adjuvant, a DNA plasmid being subsequently adsorbed. Nevertheless, the main drawback of many of these systems is a low transfection efficacy.

In view of these data, there is therefore a need to develop gene therapy drugs based on safe non-viral vectors and with a suitable transfection efficacy.

BRIEF DESCRIPTION OF THE INVENTION

The authors of the present invention have discovered that a lipid nanoparticle system incorporating a polysaccharide in its composition allows achieving an effective transfection level for transfecting genetic material into cells, as well as a high cell viability, as demonstrated by the examples performed in vitro in ARPE-19 mammal eukaryote cells.

Likewise, in vivo studies have demonstrated the capacity of this nanoparticle system to reach spleen and liver cells, effectively allowing the expression of DNA plasmids such as pCMS-EGPP, making this system potentially useful in gene therapy.

This system has also been capable of protecting the genetic material from enzyme action, particularly, from nucleases, which are present in biological fluids, which prevents its degradation or rupture in this biological medium, thus preventing the genetic material from being released from the nanoparticles before reaching their final objective.

Thus, in a first aspect the invention relates to a system for the release of biologically active molecules, comprising nanoparticles with an average particle size equal to or less than 1 micron, wherein the nanoparticles comprise:

at least one solid lipid at room temperature;
at least one cationic surfactant;
at least one non-ionic surfactant; and
at least one polysaccharide, wherein said polysaccharide comprises the bonding of at least three monosaccharides, provided that said polysaccharide is not a lipopolysaccharide, and wherein said polysaccharide is incorporated within the structure of the nanoparticles or adsorbed on the surface thereof.

In addition, it has been observed that the incorporation of the polysaccharide together with a positively charged peptide allows synergistically increasing the transfection levels when compared with a nanoparticle system which only includes the mentioned peptide or polysaccharide, as well as improving the cell viability as shown in the examples provided herein. Therefore, an additional aspect of the present invention is made up of a system such as that mentioned above which further comprises a positively charged peptide, wherein said peptide is incorporated within the structure of the nanoparticles or adsorbed on the surface thereof.

In another aspect, the invention relates to a method for the preparation of a system as has been defined above, comprising:
  (i) preparing a solution comprising the solid lipid at room temperature in an organic solvent,
  (ii) preparing an aqueous solution comprising the cationic surfactant and the non-ionic surfactant,
  (iii) adding the aqueous phase (ii) to the oily phase (i), subjecting the resulting mixture to stirring until obtaining an emulsion,
  (iv) evaporating the organic solvent,
wherein the polysaccharide, and optionally the peptide, are added to the solution (ii) or are part of an aqueous solution which is contacted with the previously formed lipid nanoparticles after performing steps (i) to (iv).

In another aspect, the invention relates to a method for the preparation of a system as has been defined above, comprising:
  (i) melting the solid lipid at room temperature,
  (ii) preparing an aqueous solution comprising the cationic surfactant and the non-ionic surfactant,
  (iii) adding the aqueous phase (ii) to the melted lipid (i), subjecting the resulting mixture to stirring until obtaining an emulsion,
  (iv) subjecting the emulsion (iii) to a homogenization process with a pressure of at least 30 psi and with at least 1 cycle,
wherein the polysaccharide, and optionally the peptide, are added to the solution (ii) or are part of an aqueous solution which is contacted with the previously formed lipid nanoparticles after performing steps (i) to (iv).

Likewise, the invention relates to a pharmaceutical or cosmetic composition comprising the nanoparticle system as has been defined above.

In another aspect, the invention relates to a nanoparticle system as has been defined above for use as a drug.

An additional aspect is made up of a nanoparticle system as has been defined above for use in the preparation of a gene therapy drug.

DESCRIPTION OF THE DRAWINGS

FIG. 1 shows the atomic force photograph. Lipid nanoparticles without any biologically active component (1A) and formulation 1 (1B).

FIG. 2 shows the photograph of formulations 1, 2 and 3 obtained by means of microscopy at 100×.

DETAILED DESCRIPTION OF THE INVENTION

Figure 3:
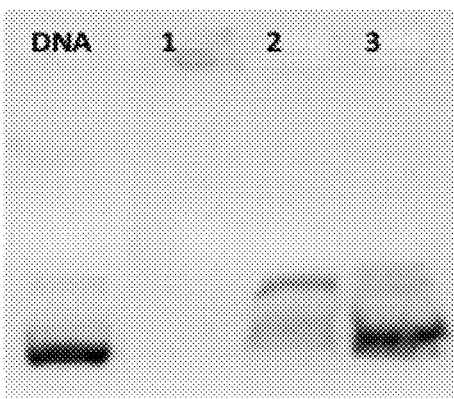
FIG. 3 shows the electrophoresis gel obtained with formulation 2 in which the genetic material condensation capacity of the nanoparticles (1), their protection capacity against DNAses (2) and their release in the presence of SDS (3) are shown.
Figure 4:
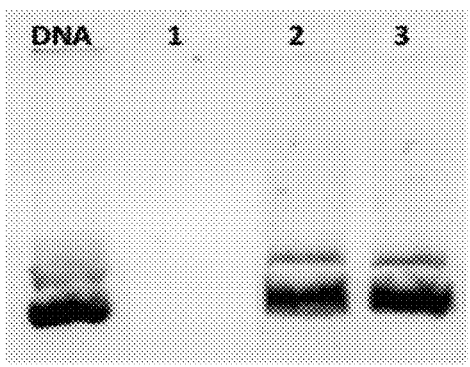
FIG. 4 shows the electrophoresis gel obtained with formulation 3 in which the genetic material condensation capacity of the nanoparticles (1), their protection capacity against DNAses (2) and their release in the presence of SDS (3) are shown.
Figure 5:
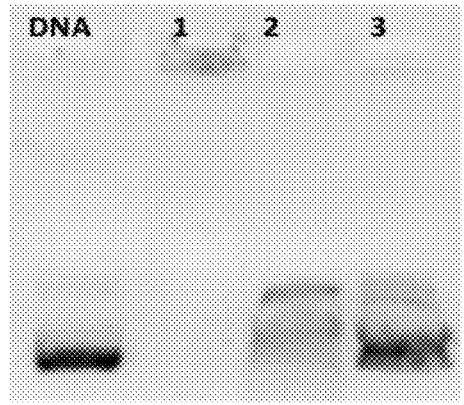
FIG. 5 shows the electrophoresis gel obtained with formulation 4 in which the genetic material condensation capacity of the nanoparticles (1), their protection capacity against DNAses (2) and their release in the presence of SDS (3) are shown.
Figure 6:
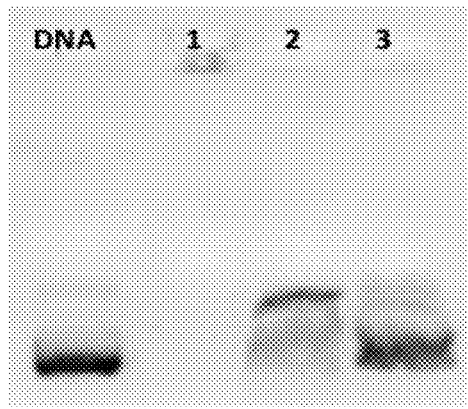
FIG. 6 shows the electrophoresis gel obtained with formulation 5 in which the genetic material condensation capacity of the nanoparticles (1), their protection capacity against DNAses (2) and their release in the presence of SDS (3) are shown.
Figure 7:
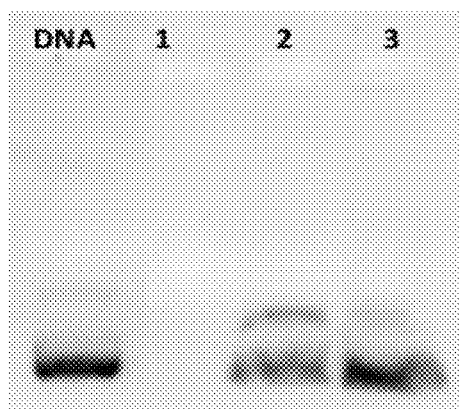
FIG. 7 shows the electrophoresis gel obtained with formulation 6 in which the genetic material condensation capacity of the nanoparticles (1), their protection capacity against DNAses (2) and their release in the presence of SDS (3) are shown.

The system of the present invention comprises nanoparticles, which have a structure comprising a lipophilic phase and a hydrophilic phase, in which a biologically active molecule can be incorporated. Said nanoparticles are in an aqueous medium although they can optionally be presented as lyophilized or desiccated products.

In the context of the present invention, the term "nanoparticle" refers to a structure comprising a lipophilic core surrounded by a hydrophilic phase encapsulating the core. The ionic interaction resulting from the different lipophilic and hydrophilic components of the nanoparticle generates independent and observable physical characteristics, the mean size of which is equal to or less than 1 μm, i.e., a mean size comprised between 1 and 1000 nm.

"Average size" is understood as the average diameter of the population of nanoparticles comprising the lipophilic phase and the hydrophilic phase. The mean size of these systems can be measured by standard methods known by the person skilled in the art, and which are described, for example, in the experimental part below.

The nanoparticles of the system of the invention are characterized by having a mean particle size equal to or less than 1 µm, they preferably have a mean size comprised between 1 and 1000 nm, more preferably between 100 and 350 nm. This size allows the nanoparticles to penetrate into the cells and administer the biologically active molecule. The mean size of the capsules is mainly influenced by the amount of the lipid component (at greater amounts the resulting size is equal or greater), by the amount of surfactants (at greater amounts or higher molecular weight the size is equal or smaller), and by the parameters of the preparation method such as the speed and type of stirring, the temperature of both phases or the duration of the mixing phase.

In addition, the nanoparticles can have a surface charge (measured by means of Z potential), the magnitude of which can vary from −50 mV to +80 mV.

Lipid Component

Nanoparticle formulation of the present invention comprises at least one solid lipid at room temperature forming part of the nanoparticle core.

In the context of the present invention, "solid lipid at room temperature" is understood as that lipid which is maintained as a solid under 45° C., being able to be saturated or unsaturated. Said definition includes triglycerides (for example tristearin), mono- or diglycerides (for example Imwitor®), fatty acids (for example stearic acid), steroids (for example cholesterol) and waxes (for example cetyl palmitate).

In a particular embodiment, the solid lipid at room temperature is selected from acylglycerides, saturated fatty acids with a chain of at least 10 carbon atoms or derivatives thereof and mixtures thereof.

The acylglycerides include both monoglycerides, diacylglycerides, triacylglycerides as well as mixtures thereof. In a preferred embodiment the acylglycerides are selected from glyceryl palmitostearate (Precirol® ATO5), glyceryl monostearate (Imwitor®900) and glyceryl behenate (Compritol® 888ATO).

In a particular embodiment, the fatty acids are saturated and have a chain of at least 10 carbon atoms. Likewise, derivatives of these fatty acids, being understood as those compounds produced as a result of the reaction of the acid group with alcohols or amines such as, for example, the esters or amides of said fatty acids, can be used. Similarly, those fatty acids, their esters or their amides having hydroxyl groups as substituents of the hydrocarbon chain are included in the definition of fatty acid derivatives.

In a preferred embodiment, glyceryl palmitostearate (Precirol® ATO5) is used as fatty acid derivative.

In another particular embodiment, the nanoparticles further comprise another lipid component, specifically a liquid lipid at temperature less than 45° C., being able to be saturated or unsaturated. The liquid lipid at room temperature is selected from unsaturated or saturated fatty acid esters, oils, fatty acids and triglycerides having a chain with less than 10 carbon atoms, and their mixtures (for example Miglyol®, soybean oil, isopropyl myristate, castor oil). In a preferred embodiment, Mygliol 212 is used as the liquid lipid.

Cationic Surfactant

The hydrophilic phase of the nanoparticles surrounding the lipophilic core comprises a cationic surfactant. The function of this component is mainly to provide the positively charged nanoparticle allowing its absorption through cationic biological environments or its adsorption thereon.

The term "cationic surfactant" is understood as that compound having a hydrophobic part and a hydrophilic part, which forms positively charged ions in a solution and allows obtaining an emulsion.

In a particular embodiment of the invention, the cationic surfactant is selected from linearly or cyclically structured primary, secondary, tertiary and quaternary ammonium salts, and mixtures thereof, such as for example pyridine, piperazine salts.

Likewise, derivatives of these ammonium salts can be used. Ammonium salts derivatives is understood as those salts incorporating at least two either primary, secondary, tertiary and/or quaternary amino groups, such as for example, guanidine, piperazine and imidazole salts in the same structure. This definition would also comprise amino acid salts, such as for example, lysine, arginine, ornithine or tryptophan salts. Likewise, this definition would encompass those ammonium salts in which the positive charge, instead of on the nitrogen atom, is on a phosphorus atom, such as for example, ditetradecyl (trimethylethylphosphonio) methylphosphonate iodide, ditetradecyl (butyldimethylphosphonio) methylphosphonate iodide, ditetradecyl (dimethylisopropylphosphonio) methylphosphonate iodide) or arsenic (ditetradecyl (trimethylarsonio) methylphosphonate iodide, dioleyl (trimethylphosphonio) methylphosphonate iodide).

In a preferred embodiment of the present invention, the ammonium salts are tetraalkylammonium salts, alkylbenzyl dimethyl ammonium salts or heterocyclic ammonium salts, more preferably are cetyltrimethylammonium bromide (CTAB), N-[1-(2,3-dioleoyloxy)propyl]-N,N,N-trimethylammonium chloride (DOTAP), or DOTMA (N-[1-(2,3-dioleyloxy)propyl]-N,N,N-trimethylammonio chloride).

Non-Ionic Surfactant

The nanoparticles additionally comprise a non-ionic surfactant the main functions of which are to control the particle size and confer stability, preventing the rupture of the latter and the formation of aggregates.

The term "non-ionic surfactant" is understood as that compound having a hydrophobic part and a hydrophilic part which allows producing an emulsion.

In a particular embodiment of the present invention the non-ionic surfactant is selected from polysorbates, polyethylene glycol copolymers and polypropylene glycol copolymers, such as for example, Tween, Span, Poloxamer.

Polysaccharide

The nanoparticle system of the present invention additionally comprises a polysaccharide the main functions of which are to facilitate the nanoparticle interaction with the cell surface and modify the nanoparticle surface charge.

This component can be part of the nanoparticle structure or can be adsorbed on the surface thereof. When the polysaccharide is part of the nanoparticle structure, the latter is in the hydrophilic phase surrounding the lipophilic core together with the cationic surfactant and the non-ionic surfactant.

Alternatively, the polysaccharide can form a complex together with the active ingredient to be incorporated into the nanoparticle formulation by means of ionic interaction. Said complex is contacted with the previously formed nanoparticles, such that the complex formed by the polysaccharide and the active ingredient is adsorbed on the surface of said nanoparticles.

In a particular embodiment, the polysaccharide is selected from chitosans, dextrans, hyaluronic acid, carrageenan, chondroitin, keratin, colominic acid, xanthan, cyclodextrins, salts, derivatives and mixtures thereof. In a preferred embodiment, the polysaccharide is selected from dextran, hyaluronic acid, carrageenan, colominic acid and heparin.

Positively Charged Peptide

The nanoparticle system of the invention can further comprise a positively charged peptide, that peptide which is ionized in a solution resulting in a net positive charge being understood as such.

The authors of the present invention have observed that the combination of the polysaccharide with the mentioned positively charged peptide allows synergistically increasing the transfection levels as well as improving the cell viability, as has been clearly shown in the transfection of the pCMS-EGFP plasmid into the human retinal pigment ARPE-19 cell line.

Like the polysaccharide, the positively charged peptide can be part of the structure of the nanoparticles or can be adsorbed on the surface thereof. When the positively charged peptide is part of the structure of the nanoparticles, the latter is in the hydrophilic phase surrounding the lipophilic core together with the cationic surfactant, the non-ionic surfactant and the polysaccharide.

Alternatively, the positively charged peptide can from a complex together with the polysaccharide and the active ingredient to be incorporated into the nanoparticle formulation. Said complex is contacted with the previously formed nanoparticles, such that the complex formed by the polysaccharide, the positively charged peptide and the active ingredient is adsorbed on the surface of said nanoparticles.

In a particular embodiment of the present invention, the positively charged peptide is selected from nuclear signaling peptides (peptides directed towards the nucleus) and mitochondrial signaling peptides (peptides directed towards the mitochondria), RGD peptides (cell surface recognition peptides containing the arginine-glycine-aspartic acid sequence and variants thereof) and CPP (cell penetrating peptides). Said peptide is preferably selected from protamines and histones.

In a variant of the invention, the system has a proportion of lipid component comprised between 0.1% and 20% by weight with respect to the total weight of the system including water, preferably between 0.5% and 5%. In another variant of the invention, when a liquid lipid at room temperature is incorporated into the nanoparticle formulation, it is in a proportion comprised between 0.1 and 5% by weight with respect to the total weight of the system including water, preferably between 0.5 and 2%.

In addition, in another variant of the invention the proportion of cationic surfactant ranges between 0.05% and 5% by weight with respect to the total weight of the system including water, preferably between 0.1% and 2%.

In anther variant of the invention, the proportion of non-ionic surfactant is preferably comprised between 0.01 and 10% by weight with respect to the total weight of the system including water, preferably between 0.1 and 3%.

In another variant of the invention, the proportion of polysaccharide is comprised between 0.01 and 10% by weight with respect to the total weight of the system including water, preferably between 0.1 and 3%.

The proportion of the positively charged peptide is in turn preferably comprised between 0.01% and 10% by weight with respect to the total weight of the system including water, more preferably between 0.1% and 3% by weight, when it is present in the formulation.

In all cases the remaining proportion mostly corresponds to purified water where the nanoparticles are dispersed. This does not mean that other ingredients such as viscosity modulators, preservatives, solubilizers, anti-flocculating agents, stabilizers, especially those which are steric or ionic or surfactant in nature, cannot be present in the nanoparticles, in the aqueous medium where they are dispersed or adsorbed thereon.

The nanoparticles of the present invention provide systems having a high capacity to associate biologically active molecules either within the nanoparticles or adsorbed thereon. Specifically, the nanoparticle system of the invention allows associating up to 100% of the active molecule when it is a plasmid. Therefore, another aspect of the invention relates to a system such as that described above which further comprises a biologically active molecule.

The term "biologically active molecule" refers to any substance which is used to treat, cure, prevent or diagnose a disease or which is used to improve the physical and mental wellbeing of human beings and animals. According to the present invention, the lipid nanoparticles developed are suitable for incorporating biologically active molecules regardless of the solubility characteristics thereof. The association capacity will depend on the molecule incorporated, but it will generally be high both for hydrophilic molecules and for very hydrophobic molecules. These molecules can include polysaccharides, proteins, peptides, lipids, hormones, antigens/allergens, according to if the objective is to generate an immune response or tolerance, nucleic acids, oligonucleotides, polynucleotides and mixtures thereof.

In a preferred embodiment of the invention the biologically active molecule is a DNA plasmid, such as pEGFP, or a nucleic acid, it is more preferably DNA, mRNA, iRNA, microRNA or an antisense sequence.

Depending on the hydrophobic or hydrophilic nature of the biologically active molecule, the latter is incorporated to the lipophilic phase or to the hydrophilic phase of the nanoparticles, respectively. Nevertheless, in a particular embodiment, the biologically active molecule can be adsorbed on the surface of the nanoparticles one the latter are formed.

The proportion of active ingredient incorporated into the nanoparticles can be as high as 20% by weight with respect to the total weight of the system including water. However, the suitable proportion will depend in each case on the active ingredient to be incorporated, the indication for use and the administration efficiency.

In the specific case of incorporating an oligonucleotide or a nucleic acid as an active ingredient, the proportion thereof in said system would be between 0.00001% and a 20% by weight with respect to the total weight of the system including water.

Another object of the present invention is a pharmaceutical composition comprising the nanoparticle system defined above and a biologically active molecule which can prevent, relieve or cure diseases.

Examples of pharmaceutical compositions include a liquid composition (i.e., suspension or dispersion of the nanoparticles of the invention) for oral, buccal, sublingual, topical, ocular, nasal or vaginal application, or any composition in the form of a gel, ointment, cream or balm for its administration by topical, ocular, nasal or vaginal route.

In a preferred aspect, the formulation is mucosally administered. The nanoparticles provide a good absorption of the drugs on the mucosa surface through their interaction with the mucosa and the cell surfaces.

In another preferred aspect, the formulation is intradermally or transdermally administered, the administration through or on skin being understood as such.

In another preferred aspect, the formulation is parentally administered.

Due to their good properties for administration on or through skin, the systems of the invention are also very suitable for cosmetic applications.

Therefore an additional object of the present invention is made up of a cosmetic composition comprising the nanoparticle system defined above. These cosmetic compositions include any liquid composition (nanoparticle suspension or dispersion) or any composition comprising the system of the invention which is in the form of a gel, cream, ointment or salve for its administration by topical route. Said compositions are characterized by having softening, protecting and healing properties, even if no cosmetically active molecule is associated thereto.

In a variant of the invention, the cosmetic composition can also incorporate active lipophilic or hydrophilic molecules which, although they do not have therapeutic effect, have cosmetic agent properties. The following should be mentioned among the active molecules which can be incorporated into the nanoparticles, softening agents, preservatives, aromatic substances, anti-acne agents, antifungal agents, antioxidants, deodorants, antiperspirants, antidandruff, depigmenting agents, antiseborrheic agents, colorants, bronzers, UV light absorbers, enzymes, flavoring substances, among others.

The pharmaceutical and cosmetic compositions can further comprise pH controlling agents such as for example buffer agents which prevent the pH of the composition from dropping to values less than 5, antioxidant agents which inhibit the oxidation of the lipid component, as well as preservatives which prevent important structural changes in the formulation.

Depending on their function, these additional components can be present in the phases making up the nanoparticles or in the aqueous medium where they are dispersed or completely or partially adsorbed thereon. The person skilled in the art can determine what additional components can be used and if they are necessary, many of them being commonly used in pharmaceutical and cosmetic compositions.

An additional aspect of the present invention is made up of a method [hereinafter method 1] for the preparation of the system of the invention, as has been defined above, comprising the nanoparticles. Said method 1 comprises a first step of preparing the lipid phase by means of dissolving the solid lipid at room temperature in an organic solvent, wherein the proportion of the lipid component is at least 0.1% by weight with respect to the total weight of the organic solution, it is preferably comprised between 0.1 and 40% by weight.

In a particular embodiment, when the biologically active molecule to be incorporated in the nanoparticles is a lipophilic molecule and it is furthermore to be incorporated into the structure of the nanoparticles, said active molecule is dissolved together with the lipid in the organic solvent.

The choice of the organic solvent depends in a large extent on both the lipid component and, where appropriate, on the active ingredient incorporated. Regardless of the above, the use of pharmaceutically acceptable organic solvents and the use of the smallest possible amount are preferred due to the fact that it will have to subsequently be removed in the final step of the method which leads to the nanoparticle production.

In a particular embodiment of the invention, the organic solvent is selected from dichloromethane, acetone, chloroform, it is more preferably dichloromethane. The proportion of the organic solvent can range between 1 and 60% by weight with respect to the total weight of the system including water, more preferably it ranges between 10 and 30% by weight.

In another particular embodiment, a liquid lipid at room temperature as has been mentioned above can be added to the lipophilic phase.

A second step of method 1 consists of dissolving the cationic surfactant and the non-ionic surfactant in water. The polysaccharide can additionally be dissolved in this aqueous phase together with the surfactants, as well as the positively charged peptide when the latter is present in the nanoparticle formulation.

In a particular embodiment, when the biologically active molecule to be incorporated into the nanoparticles is a hydrophilic molecule and it is furthermore to be incorporated into the structure of the nanoparticles, said active molecule is dissolved together with the rest of the components of the aqueous phase in the water.

Once both solutions are prepared, the aqueous phase is added to the lipid phase. The order of addition must be the one indicated for the purpose of obtaining the external aqueous phase emulsion. The resulting mixture is subjected to a rigorous stirring until obtaining an emulsion.

Subsequently, the organic solvent is evaporated by means of any method known by a person skilled in the art. In a particular embodiment, the organic solvent evaporation step is carried out by keeping the emulsion under mechanical stirring for at least five minutes, subsequently subjecting it to vacuum for at least five minutes. After removing the organic solvent, the lipid phase solidifies, a nanoparticle suspension thus being obtained.

In a particular embodiment, method 1 further comprises a step of cooling the nanoparticle suspension to a temperature comprised between 4 and 8° C. and the subsequent filtration by centrifugation to finally resuspend the nanoparticles in purified water.

In another additional aspect, the invention relates to a method [hereinafter method 2] for the preparation of the system of the invention, as has been defined above, comprising the nanoparticles. Said method 2 comprises a first step of preparing the lipid phase in which the solid lipid at room temperature is melted at a temperature greater than its melting point.

In a particular embodiment, when the biologically active molecule to be incorporated in the nanoparticles is a lipophilic molecule and it is furthermore to be incorporated into the structure of the nanoparticles, said active molecule is dissolved in the melted lipid.

In another particular embodiment, a liquid lipid at room temperature is added to the melted lipid.

A second step of method 2 consists of dissolving the cationic surfactant and the non-ionic surfactant in water. The polysaccharide can additionally be dissolved in this aqueous phase together with the surfactants, as well as the positively charged peptide when the latter is present in the nanoparticle formulation.

In a particular embodiment, when the biologically active molecule to be incorporated in the nanoparticles is a lipophilic molecule and it is furthermore to be incorporated into the structure of the nanoparticles, said active molecule is dissolved together with the rest of the components of the aqueous phase in the water.

Once both phases are prepared, the aqueous phase is added to the lipid phase. The order of addition must be the one indicated for the purpose of obtaining the external aqueous phase emulsion. The resulting mixture is subjected to a rigorous stirring until obtaining an emulsion.

Subsequently, the resulting emulsion is subjected to a step of homogenizing by means of any method known by a person skilled in the art, for the purpose of obtaining particles with a size comprised in the nanometer range, i.e., up to a size equal to or less than 1 μm.

"Homogenization" is understood as any process which allows reducing, by mechanical means, the size of the globules formed in the emulsion resulting from carrying out steps i) to iii) of method 2 of the invention. Examples of homogenization methods include high pressure homogenization, sonication, high-shear mixing or the application of mechanical stress or impact forces.

In a particular embodiment, the homogenization process is carried out by means of hot high pressure homogenization with a pressure of at least 30 psi and with at least one cycle.

In a particular embodiment, method 2 further comprises a step of cooling the nanoparticle suspension to a temperature comprised between 4 and 8° C. and the subsequent filtration by centrifugation to finally resuspend the nanoparticles in purified water.

In a particular embodiment, the biologically active molecule is not incorporated into the structure of the nanoparticle but is adsorbed on the surface of the lipid nanoparticles. To that end, said active molecule is dissolved in an aqueous solution which is subsequently contacted with the lipid nanoparticles previously obtained according to any of the two methods described above. Preferably, the contact is performed at room temperature for at least five minutes for the purpose of obtaining a non-viral vector comprising the lipid nanoparticles on the surface of which the biologically active molecule is adsorbed.

In another particular embodiment, the polysaccharide and, optionally, the positively charged peptide when the latter is present in the formulation, are adsorbed on the surface of the nanoparticles together with the biologically active molecule. To that end, once the lipid nanoparticles are obtained by any of the two methods described above, a complex comprising the polysaccharide, the active ingredient and optionally the positively charged peptide is prepared by means of contacting aqueous solutions comprising, each of them, the three mentioned components. Once said complex is obtained, the latter is contacted with the previously obtained lipid nanoparticles for finally obtaining the non-viral vector comprising the lipid nanoparticles on the surface of which the polysaccharide, the biologically active molecule and, where appropriate, the positively charged peptide are adsorbed.

Other ingredients can additionally be added to the nanoparticle system as has been described above such as viscosity modulators, preservatives, solubilizers, anti-flocculating agents, stabilizers, especially those which are steric or ionic or surfactant in nature. These components will be added to the lipophilic or hydrophilic phase depending on their nature.

Some illustrative examples which clearly show the features and advantages of the invention are described below, nevertheless, they must not be interpreted as limiting the object of the invention as defined in the claims.

EXAMPLES

The nanoparticles obtained have been characterized by means of their average size, their surface charge and their capacity for incorporating genetic material. The common methods used for said characterization are detailed below:

1. Morphology

The different formulations were observed by fluorescence microscopy using a Nikon Eclipse TE 2000-S equipment. Nanoparticles without biologically active substance and formulation 1 were observed by atomic force microscopy (AFM) using the Multimode™ (Digital Instruments) mode. The images were captured in Tapping Mode™ using a silicone cantilever (RTESP, rotated tapping etched silicon probe type) with a resonance frequency of approximately 300 kHz.

2. Particle Size and Surface Charge

The particle size of all the formulations was measured by means of photon correlation spectroscopy. The surface charge was measured by means of laser doppler velocimetry. Both parameters were measured with a Zetasizer 3000.

3. Genetic Material Nanoparticle Binding Capacity.

The DNA nanoparticle condensation capacity was determined by means of agarose gel electrophoresis with 1% of ethidium bromide for 30 minutes at 120 V. The bands were observed in a TFX-20 M (Vilber-Lourmat) transilluminator. The images were captured using a digital camera (Bio-Rad, DigicDoc, model).

Example 1. Preparation of Nanoparticles without Polysaccharide or Peptide by Means of the Solvent Emulsification/Evaporation Technique (Formulation 1)

A 5% precirol solution in dichloromethane (2 mL) is prepared. In addition an aqueous solution (10 mL) of 0.4% DOTAP and 0.1% Tween 80 is prepared. The aqueous phase is added to the oily phase, subjecting the mixture to a rigorous stirring until obtaining an emulsion. Then the organic solvent is evaporated, keeping the emulsion under mechanical stirring for at least 5 minutes, subsequently subjecting it to vacuum for at least 5 minutes. The lipid thus precipitates, a nanoparticle suspension being obtained. After cooling to a temperature between 4 and 8° C., they are filtered by centrifugation and resuspended in purified water.

For preparing the complexes with the genetic material a 1 μg/μL plasmid (pCMS-EGFP) solution in distilled water is prepared. The nanoparticle suspension is then contacted with the solution containing the genetic material at a 5:1 ratio (expressed as the weight/weight ratio between DOTAP and DNA) and is kept under stirring for 15 minutes at room temperature.

FIG. 1 shows an atomic force photograph of the lipid nanoparticles without biologically active component and of formulation 1.

Example 2. Preparation of Nanoparticles with Polysaccharide and without Peptide by Means of the Solvent Emulsification/Evaporation Technique (Formulation 2)

Lipid Nanoparticles:

A 5% precirol solution in dichloromethane is prepared. In addition an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Dextran:pCMS-EGFP Complexes:

An aqueous solution is prepared by means of dissolving pCMS-EGFP plasmid (1 μg/μL) in distilled water. in addition another aqueous solution is prepared by means of dissolving dextran (1 μg/μL) having a molecular weight of approximately 3200 (supplied by Sigma) in distilled water.

The two solutions with a dextran:pCMS-EGFP ratio of 5:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 3. Preparation of Nanoparticles with Polysaccharide and with Peptide by Means of the Solvent Emulsification/Evaporation Technique (Formulation 3)

Lipid Nanoparticles:

A 5% precirol solution in dichloromethane is prepared. In addition an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 time at 3000 rpm for 20 minutes using Amicon® Ultra (Millipore) filters.

Dextran:Protamine:pCMS-EGFP Complexes:

An aqueous solution is prepared by means of dissolving the pCMS-EGFP plasmid (1 μg/μL) in distilled water. In addition, another aqueous solution is prepared by means of dissolving dextran (1 μg/μL) having a molecular weight of approximately 3200 (supplied by Sigma) in distilled water. Another aqueous solution is additionally prepared by means of dissolving protamine (1 μg/μL) in distilled water.

The three solutions with a dextran:protamine:pCMS-EGFP ratio of 1:2:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

FIG. 2 shows the photographs corresponding to formulations 1, 2 and 3 obtained by means of microscopy at 100×. The spherical shape of the particles and their homogeneous size can be observed in all cases, there being no apparent differences between the three formulations.

Example 4. Preparation of Nanoparticles without Polysaccharide or Peptide by Means the High Pressure Homogenization Technique (Formulation 4)

100 mg of precirol are melted by heating at 70° C. In addition an aqueous solution of 0.4% DOTAP and 0.1% Tween 80 is prepared. A pre-emulsion is prepared by adding the aqueous phase (10 mL) to the melted lipid, subjecting the mixture to vigorous stirring until obtaining an emulsion. Then the mixture is subjected to hot high pressure homogenization with a pressure of at least 30 psi and with at least 1 cycle. After cooling in a refrigerator (4-8° C.) for 15 minutes, the nanoparticles obtained are washed by centrifuging 3 times at 3000 rpm for 20 minutes using Amicon® Ultra (Millipore) filters.

Example 5. Preparation of Nanoparticles with Polysaccharide and without Peptide by Means of the High Pressure Homogenization Technique (Formulation 5)

Lipid Nanoparticles:

100 mg of precirol are melted by heating at 70° C. In addition an aqueous solution of 0.4% DOTAP and 0.1% Tween 80 is prepared. A pre-emulsion is prepared by adding the aqueous phase (10 mL) to the melted lipid, subjecting the mixture to vigorous stirring until obtaining an emulsion. Then the mixture is subjected to hot high pressure homogenization with a pressure of at least 30 psi and with at least 1 cycle. After cooling in a refrigerator (4-8° C.) for 15 minutes, the nanoparticles obtained are washed by centrifuging 3 times at 3000 rpm for 20 minutes using Amicon® Ultra (Millipore) filters.

Dextran:pCMS-EGFP Complexes:

An aqueous solution is prepared by means of dissolving pCMS-EGFP plasmid (1 μg/μL) in distilled water. In addition, another aqueous solution is prepared by means of dissolving dextran (1 μg/μL) of approximately 3200 (supplied by Sigma) in distilled water.

The two solutions with a dextran:pCMS-EGFP ratio of 5:1 are contacted and kept under stirring for 30 minutes at room temperature.

Then the nanoparticle suspension is contacted with the solution containing the complex formed with the genetic material, at a 5:1 ratio (expressed as the weight/weight ratio between DOTAP and DNA) and is kept under stirring for 15 minutes at room temperature.

Example 6. Preparation of Nanoparticles with Polysaccharide and with Peptide by Means of the High Pressure Homogenization Technique (Formulation 6)

Lipid Nanoparticles:

100 mg of precirol are melted by heating at 70° C. in addition, an aqueous solution of 0.4% DOTAP and 0.1% Tween 80 is prepared. A pre-emulsion is prepared by adding the aqueous phase (10 mL) to the melted lipid, subjecting the mixture to vigorous stirring until obtaining an emulsion. Then the mixture is subjected to hot high pressure homogenization with a pressure of at least 30 psi and with at least 1 cycle. After cooling in a refrigerator (4-8° C.) for 15 minutes, the nanoparticles obtained are washed by centrifuging 3 times at 3000 rpm for 20 minutes using Amicon® Ultra (Millipore) filters.

Dextran:Protamine:pCMS-EGFP Complexes:

An aqueous solution is prepared by means of dissolving pCMS-EGFP plasmid (1 μg/μL) in distilled water. In addition, another aqueous solution is prepared by means of dissolving dextran of approximately 3200 (supplied by Sigma) (1 μg/μL) in distilled water. Additionally another aqueous solution is prepared by means of dissolving protamine (1 μg/μL) in distilled water.

The three solutions with a dextran:protamine:pCMS-EGFP ratio of 1:2:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Table I shows the particle size and the surface charge of the 6 formulations above:

| Formulation | Particle size (nm) | Surface charge (mV) |
| --- | --- | --- |
| Formulation 1 | 308 ± 6.8 | +32.4 ± 0.5 |
| Formulation 2 | 311 ± 20.1 | +32 ± 1.8 |
| Formulation 3 | 248.5 ± 7.87 | +38 ± 1.0 |
| Formulation 4 | 224.7 ± 2.61 | +31.2 ± 4.2 |
| Formulation 5 | 226.3 ± 3.04 | +29.8 ± 2.3 |
| Formulation 6 | 210 ± 3.62 | +34.2 ± 2.8 |

Example 7. Preparation of Nanoparticles with Polysaccharide and with Peptide by Means of the Solvent Emulsification/Evaporation Technique (Formulation 7)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Dextran:Protamine:pCMS-EGFP Complexes:

An aqueous solution is prepared by means of dissolving pCMS-EGFP plasmid (1 µg/µL) in distilled water. In addition, another aqueous solution is prepared by means of dissolving dextran having a molecular weight of approximately 8000 (supplied by Sigma) (1 µg/µL) in distilled water. Additionally another aqueous solution is prepared by means of dissolving protamine (1 µg/µL) in distilled water.

The three solutions with a dextran:protamine:pCMS-EGFP ratio of 1:3:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 8. Preparation of Nanoparticles with Polysaccharide and with Peptide by Means of the Solvent Emulsification/Evaporation Technique (Formulation 8)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Dextran:Protamine:pCMS-EGFP Complexes:

An aqueous solution is prepared by means of dissolving pCMS-EGFP plasmid (1 µg/µL) in distilled water. In addition, another aqueous solution is prepared by means of dissolving dextran having a molecular weight of approximately 1000 (supplied by Sigma) (1 µg/µL) in distilled water. Additionally another aqueous solution is prepared by means of dissolving protamine (1 µg/µL) in distilled water.

The three solutions with a dextran:protamine:pCMS-EGFP ratio of 3:1:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 9. Preparation of Nanoparticles with Polysaccharide and with Peptide by Means of the Solvent Emulsification/Evaporation Technique (Formulation 9)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Carrageenan:Protamine:pCMS-EGFP Complexes:

An aqueous solution is prepared by means of dissolving pCMS-EGFP plasmid (1 µg/µL) in distilled water. In addition, another aqueous solution is prepared by means of dissolving carrageenan (1 µg/µL) in distilled water. Additionally, another aqueous solution is prepared by means of dissolving protamine (1 µg/µL) in distilled water.

The three solutions with a carrageenan:protamine:pCMS-EGFP ratio of 0.5:2:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 10. Preparation of Nanoparticles with Polysaccharide and with Peptide by Means of the Solvent Emulsification/Evaporation Technique (Formulation 10)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Colominic Acid:Protamine:pCMS-EGFP Complexes:

An aqueous solution is prepared by means of dissolving pCMS-EGFP plasmid (1 µg/µL) in distilled water. In addition, another aqueous solution is prepared by means of dissolving colominic acid (1 µg/µL) in distilled water. Additionally another aqueous solution is prepared by means of dissolving protamine (1 µg/µL) in distilled water.

The three solutions with a colominic acid:protamine:pCMS-EGFP ratio of 0.5:2:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 11. Preparation of Nanoparticles with Polysaccharide and with Peptide by Means of the Solvent Emulsification/Evaporation Technique (Formulation 11)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Hyaluronic Acid:Protamine:pCMS-EGFP Complexes:

An aqueous solution is prepared by means of dissolving pCMS-EGFP plasmid (1 µg/µL) in distilled water. In addition, another aqueous solution is prepared by means of dissolving hyaluronic acid (1 µg/µL) in distilled water. Additionally, another aqueous solution is prepared by means of dissolving protamine (1 µg/µL) in distilled water.

The three solutions with a hyaluronic acid:protamine:pCMS-EGFP ratio of 0.1:2:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 12. Preparation of Nanoparticles with Polysaccharide and with Peptide by Means of the Solvent Emulsification/Evaporation Technique (Formulation 12)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Heparin:Protamine:pCMS-EGFP Complexes:

An aqueous solution is prepared by means of dissolving pCMS-EGFP plasmid (1 µg/µL) in distilled water. In addition, another aqueous solution is prepared by means of dissolving heparin (1 µg/µL) in distilled water. Additionally, another aqueous solution is prepared by means of dissolving protamine (1 µg/µL) in distilled water.

The three solutions with a heparin:protamine:pCMS-EGFP of ratio 0.1:2:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 13. Preparation of Nanoparticles with Polysaccharide and without Peptide by Means of the Solvent Emulsification/Evaporation Technique (Formulation 13)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Hyaluronic Acid:pCMS-EGFP Complexes:

An aqueous solution is prepared by means of dissolving pCMS-EGFP plasmid (1 µg/µL) in distilled water. In addition, another aqueous solution is prepared by means of dissolving hyaluronic acid (1 µg/µL) in distilled water.

The two solutions with a hyaluronic acid:pCMS-EGFP ratio of 0.1:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 14. Preparation of Nanoparticles with Polysaccharide and without Peptide by Means of the Solvent Emulsification/Evaporation Technique (Formulation 14)

Lipid Nanoparticles:

A 5% precirol solution in dichloromethane is prepared. In addition, an aqueous solution of 0.4% DOTAP and 0.1% Tween 80 is prepared. The aqueous phase is added to the oily phase at a 1:5 ratio and the mixture is subjected to sonication (Branson Sonifier 250, Danbury) for 30 seconds at 50 W. Then the organic solvent is evaporated, keeping the emulsion under mechanical stirring for 5 minutes, subsequently subjecting it to vacuum for 15 minutes. After cooling in a refrigerator (4-8° C.) for 15 minutes, the nanoparticles obtained are washed by centrifuging 3 times at 3000 rpm for 20 minutes using Amicon® Ultra (Millipore) filters.

Low Molecular Weight Heparin:pCMS-EGFP Complexes:

An aqueous solution is prepared by means of dissolving pCMS-EGFP plasmid (1 µg/µL) in distilled water. In addition, another aqueous solution is prepared by means of dissolving low molecular weight heparin (1 µg/µL) in distilled water.

The two solutions with a low molecular weight heparin: pCMS-EGFP ratio of 0.1:1 are contacted and kept under stirring for 30 minutes at room temperature.

Then the nanoparticle suspension is contacted with the solution containing the complex formed with the genetic material at a 5:1 ratio (expressed as the weight/weight ratio between DOTAP and DNA) and is kept under stirring for 15 minutes at room temperature.

Example 15. Protection Capacity for Protecting DNA Against DNAse I and Induced Release with SDS To know the protection capacity of the formulations over DNA, the deoxyribonuclease I (DNAse I) enzyme which is capable of hydrolyzing DNA molecules was used. Formulations 1-6 were contacted with DNAse for 30 minutes at 37° C. 1 U of DNAse was used for each 2.5 µg of DNA. After 30 minutes, sodium lauryl sulfate (SDS) was added until a final concentration of 1% to stop the action of the enzyme and to release the DNA of the samples. The samples are subsequently analyzed in an agarose gel as has been defined above in the common methods.

FIGS. 3 to 7 show the electrophoresis gels showing the DNA condensation capacity, the protection capacity against DNAses and the induced release by SDS.

It can be confirmed that both the nanoparticles containing the polysaccharide and those containing the polysaccharide-peptide combination are capable of condensing the DNA, of protecting it against DNAse and furthermore, the DNA is capable of being released from the complex.

Example 16. In Vitro Assays of Cell Transfection Capacity of Formulations 1 to 14

The in vitro evaluation of formulations 1-14 was carried out in the ARPE-19 cell line (human retinal pigment epithelial cells). These cells were kept in culture in Dulbecco's MEM medium: Ham's Nutrient Mixture F-12, 1:1 Mix (DMEM: F-12) with 10% fetal bovine serum, 0.2% Normocin antibiotic and penicillin. The cell cultures are kept at 37° C. in a 5% $CO_2$ air atmosphere, changing the medium every 2 or 3 days. The transfection studies were conducted in 24-well plates with densities of 30,000 cells per well and they were incubated until they reached 80-90% of confluence. Then part of the medium was removed, leaving the volume necessary for covering the entire well, then adding the formulation to be studied. They were incubated for 4 hours and then more medium volume was added. The amount of vectors which was added to each well was equivalent to 2.5 µg of DNA.

The cell viability and transfection was evaluated by means of flow cytometry (FACSCalibur™, Becton Dickinson Biosciences, San Jose, USA). The fluorescence due to the EGFP was measured at 525 nm (FL1). For each sample, 10,000 events were used. The cell viability was analyzed using the BD Via-Probe™ kit. This kit contains 7-aminoactinomycin (7-AAD) reagent used for the exclusion of nonviable cells, producing fluorescence in contact with the dead cells. The fluorescence due to 7-AAD corresponding to the nonviable cells, was measured at 650 nm (FL3), 10,000 events being taken per sample. Cells subjected to common culture conditions were used as control. Viabilities greater than 80%, a value similar to that obtained with the controls (cells without transfection) were obtained with all the formulations; this indicates an apparent absence of toxicity. In addition, the inclusion of polysaccharide (formulation 2) and peptide+polysaccharide combination (formulation 3), increases the viability with respect to the formulation not including those components (formulation 1). The differences are more notable for formulation 3.

Figure 8:
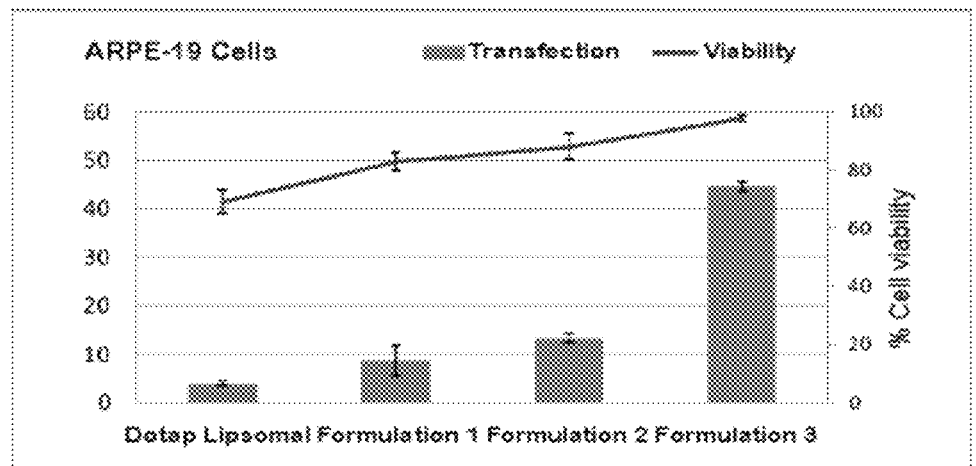
FIG. 8 shows the in vitro cell viability and transfection level of formulations 1, 2, 3 and DOTAP liposomal in ARPE-19 cells.
Figure 9:
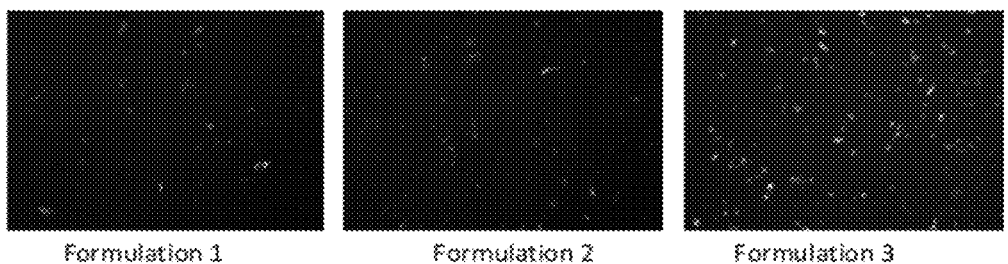
FIG. 9 shows the fluorescence microscopy photograph showing the in vitro cell viability and transfection level of formulations 1, 2, 3.
Figure 10:
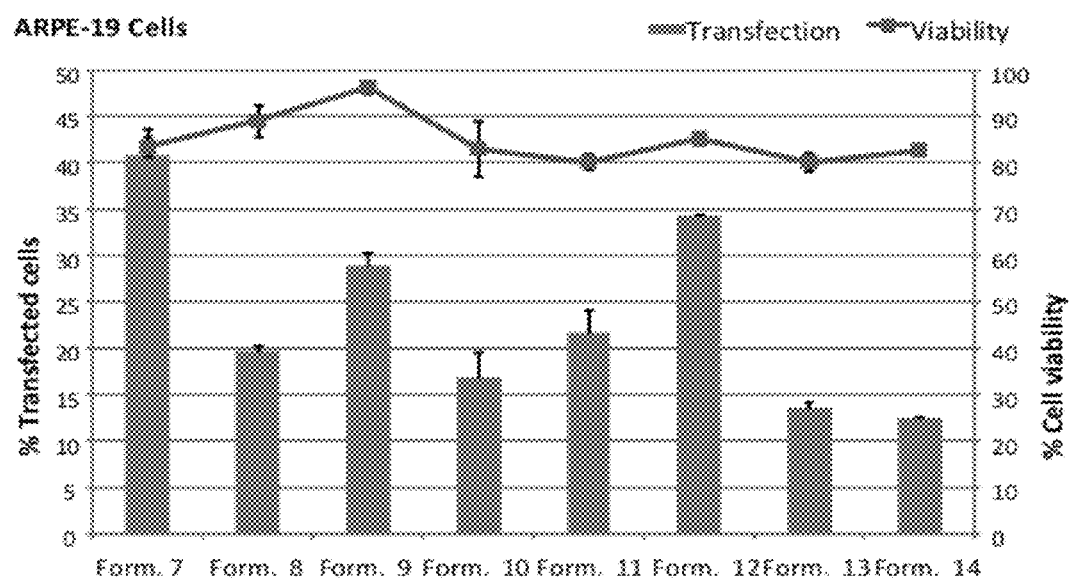
FIG. 10 shows the in vitro cell viability and transfection level of formulations 7-14 in ARPE-19 endothelial cells.

The transfection studies were carried out in ARPE-19 cells. The percentage of transfected cells (positive EGFP cells %) and the cell viability was measured by means of flow cytometry. FIGS. 8 and 9 show the results corresponding to the cell viability and transfection studies in the ARPE-19 cells for formulations 1 to 3, whereas FIG. 10 shows the results corresponding to the cell viability and transfection studies in the ARPE-19 cells for formulations 7 to 14. A study was conducted with DOTAP liposomal as control.

As can be confirmed, the incorporation of a polysaccharide in the formulation increases the transfection with respect to the control group (nanoparticles without polysaccharide or peptide). Nevertheless, the incorporation of a polysaccharide and a peptide in the formulation allows synergistically increasing the transfection levels when compared with a nanoparticle system only including the mentioned polysaccharide, as well as improving the cell viability.

Example 17. In Vivo Assays of Nanoparticle Transfection Capacity

To know the nanoparticle transfection capacity, an in vivo study was carried out which consisted of administering the formulations to Balb/c mice intravenously.

Formulation 1 and formulation 3 were administered. The administration was made through the tail vein, the formulation being injected in a volume of 100 µL, corresponding to a 60 µg pCMS-EGFP plasmid dose. Mice which have been administered with free plasmid and plasmid-free nanoparticles were used as control groups. At 3 and 7 days after the administration, the animals were sacrificed and the lung, liver and spleen were extracted. The organs were placed in freezing medium (Jung, Leica), they were froze with liquid nitrogen and subsequently sectioned by means of a cryostat (Cryocut 3,000, Leica). Each group was made up of 3 animals. 12 sections were obtained from each organ.

The sections (7-10 µm) were fixed with 4% paraformaldehyde for 10 minutes at room temperature. After washing them in PBS, the sections were treated with Triton® X-10 and 2% goat serum (NGS) in 1M PBS for 1 hour at room temperature. Subsequently, the sections were incubated with a primary antibody (anti-GFP polyclonal antibody) for 2 hours at room temperature. After a phase of washing with PBS, they were incubated with the secondary antibody (Alexa Fluor® 488 goat anti-rabbit IgG) for 45 minutes at room temperature. Finally, the sections were again washed with PBS and coated with Fluoromount G.

Figure 11:
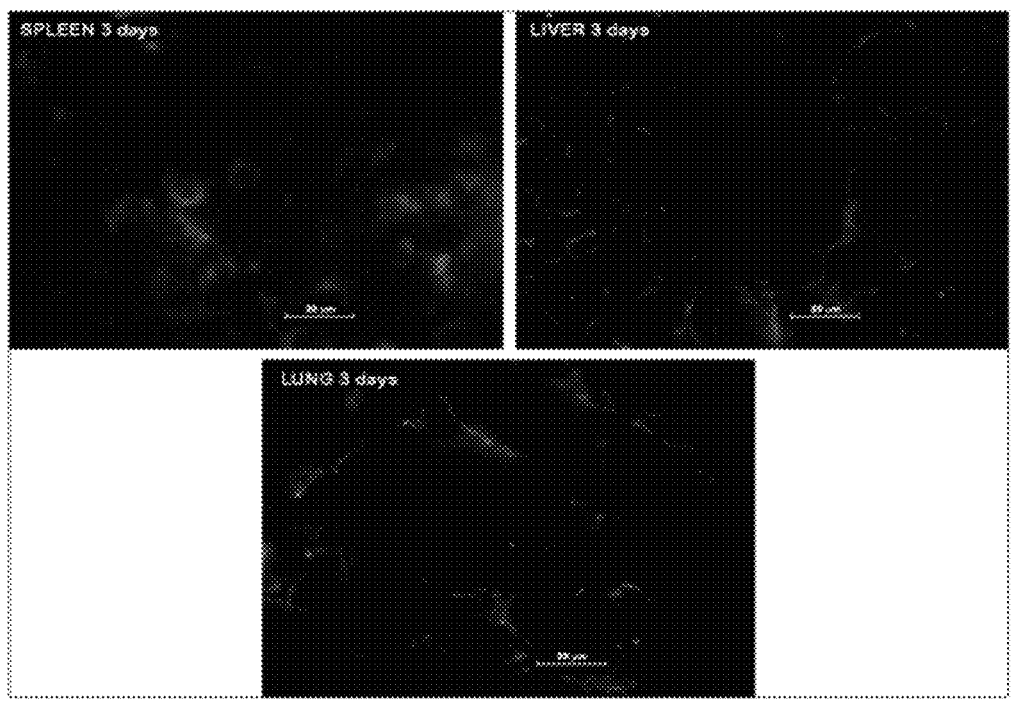
FIG. 11 shows the fluorescence microscopy photograph of mouse spleen, liver and lung samples in which the pCMS-EGFP expression after the administration of formulation 3 endovenously to mice is shown.

FIG. 11 shows the fluorescence microscopy photographs of mouse spleen, liver and lung samples obtained by means of an inverted fluorescence microscope (eclipse TE2000-S, Nikon) in which the pCMS-EGFP expression after the administration of formulation 3 endovenously to mice is shown.

The following table shows the transfection obtained with the different formulations:

| Time | Liver | Spleen | Lung |
|---|---|---|---|
| | Formulation 1 | | |
| 3 days | 100% sections | 100% sections | — |
| 7 days | 17% sections | 17% sections | — |
| | Formulation 3 | | |
| 3 days | 84.6% sections | 100% sections | 66.7% sections |
| 7 days | 37.5% sections | 100% sections | 60% sections |

These results indicate that the formulations are capable of transfecting, in vivo, liver, spleen and lung cells. Depending on the composition, different transfection levels are obtained in the different tissues studied. The inclusion of the peptide+polysaccharide combination significantly increases the transfection levels and the duration thereof, with respect to the formulation free of these components.

Example 18. In Vitro Assays of the Nanoparticle Entry into Different Cell Lines The in vitro evaluation of formulation 3 entry was carried out in the following cell lines: ARPE-19 (human retinal pigment epithelial cells), HEK-293 (human embryonic kidney cells), HepG2 (human hepatocellular liver carcinoma cells), and Ea.Hy926 (human endothelial cells).

These cells were kept in culture in their corresponding media. The cell cultures were kept at 37° C. in 5% $CO_2$ air atmosphere, changing the medium every 2 or 3 days. The entry studies were conducted by adding the formulation prepared with the pCMS-EGFP plasmid labeled with ethidium monoazide (EMA) which emits red fluorescence. Once the cells reached the suitable confluence (60-70%) part of the medium was removed, leaving the volume necessary for covering the cells, then adding the formulation to be studied. They were incubated for 4 hours and then more medium volume was added. The amount of vectors which was added to each well was equivalent to 2.5 μg of DNA.

The intake was measured by means of flow cytometry (FACSCalibur™, Becton Dickinson Biosciences, San Jose, USA), determining the percentage of cells which captured the vectors 24 hours after adding the vectors. The fluorescence due to EMA was measured at 650 nm (FL3), 10,000 events being taken per sample. Cells subjected to the common culture conditions were used as control.

The following table shows the percentage of each cell line which captured the vectors:

| Cell line | Formulation 3 |
|---|---|
| ARPE-19 | 69.28 ± 23.97 |
| HEK-293 | 39.61 ± 15.05 |
| HepG2 | 43.31 ± 1.61 |
| Ea.Hy926 | 21.78 ± 1.02 |

As can be confirmed, the vectors are capable of entering into cell lines of different origins.

Example 19. In Vitro Assays of Nanoparticle Cell Transfection Capacity Over Time The in vitro evaluation of formulation 3 was carried out in the Ea.Hy926 (human endothelial cells) cell line. These cells were kept in culture in Dulbecco's Modified Eagle Medium (D-MEM)-High Glucose supplemented with 10% fetal bovine serum and 0.2% Normocin antibiotic. The cell cultures were kept at 37° C. in a 5% $CO_2$ air atmosphere, changing the medium every 2 or 3 days. The transfection studies were conducted in 24-well plates with densities of 50,000 cells per well and they were incubated until they reached 80-90% of confluence. Then part of the medium was removed, leaving the volume necessary for covering the entire well, then adding the formulation to be studied. They were incubated for 4 hours and then more medium volume was added. The amount of vectors which was added to each well was equivalent to 2.5 μg of DNA.

The cell viability and transfection was evaluated by means of flow cytometry (FACSCalibur™, Becton Dickinson Biosciences, San Jose, USA). The fluorescence due to the EGFP was measured at 525 nm (FL1). For each sample, 10,000 events were used. The cell viability was analyzed using the BD Via-Probe™ kit. This kit contains 7-aminoactinomycin (7-AAD) reagent used for the exclusion of nonviable cells, producing fluorescence in contact with the dead cells. The fluorescence due to 7-AAD corresponding to the nonviable cells, was measured at 650 nm (FL3), 10,000 events being taken per sample. Cells subjected to at common culture conditions were used as control.

Figure 12:
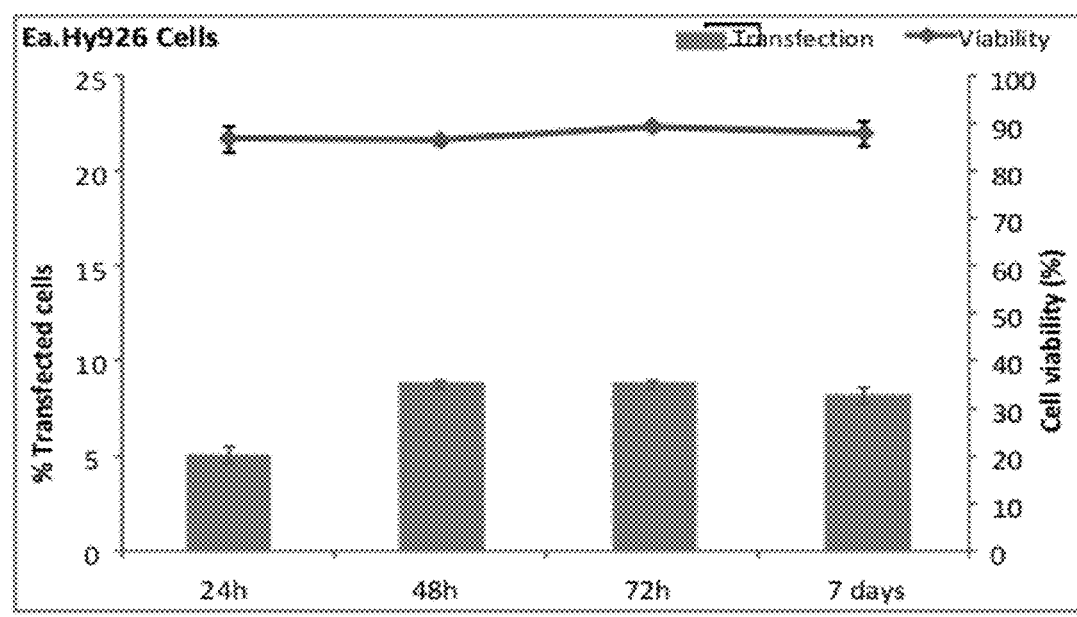
FIG. 12 shows the in vitro cell viability and transfection level of formulation 3 in Ea.Hy926 endothelial cells over time.

The transfection studies were carried out in Ea.Hy926 cells. The percentage of transfected cells (positives EGFP cells %) and the cell viability was measured by means of flow cytometry. FIG. 12 shows the results corresponding to the cell viability and transfection studies in the Ea.Hy926 cells between 24 hours and 7 days with formulation 3.

As can be confirmed, transfection occurs in the Ea.Hy926 cells after 24 hours. The transfection increases after 48 hours, and is maintained for at least 7 days.

Viabilities greater than 80%, a value similar to that obtained with the controls (cells without transfection) were obtained with all of the formulations; this indicates an apparent absence of toxicity.

The invention claimed is:

1. A system for the release of biologically active molecules comprising nanoparticles with an average particle size equal to or less than 1 micron, wherein the nanoparticles have a structure comprising:
  a lipophilic core comprising at least one solid lipid at room temperature;
  a hydrophilic phase surrounding the lipophilic core, said hydrophilic phase comprising at least one cationic surfactant and at least one non-ionic surfactant;
  at least one biologically active molecule, wherein the biologically active molecule is selected from the group consisting of nucleic acids, oligonucleotides, polynucleotides and mixtures thereof; and
  at least one polysaccharide, wherein the polysaccharide is selected from the group consisting of chitosans, dextrans, hyaluronic acid, carrageenan, chondroitin, keratin, colominic acid, xanthan, cyclodextrins, salts or derivatives of polysaccharides selected from chitosans, dextrans, hyaluronic acid, carrageenan, chondroitin, keratin, colominic acid, xanthan or cyclodextrins, and mixtures thereof;
  wherein said polysaccharide comprises the bonding of at least three monosaccharides, provided that said polysaccharide is not a lipopolysaccharide, and
  wherein said polysaccharide is either incorporated in the hydrophilic phase of the nanoparticles or forms a complex together with the biologically active molecule, said complex being adsorbed on the surface of the nanoparticles.

2. The system according to claim 1, further comprising at least one peptide with a net positive charge.

3. The system according to claim 1, wherein the solid lipid at room temperature is selected from the group consisting of monoglycerides, diacylglycerides, triacylglycerides and mixtures thereof.

4. The system according to claim 1, wherein the cationic surfactant is selected from the group consisting of linearly or cyclically structured primary, secondary, tertiary and quaternary ammonium salts, mixtures thereof and derivatives thereof.

5. The system according to claim 1, wherein the non-ionic surfactant is selected from the group consisting of polysorbates, polyethylene glycol copolymers, polypropylene glycol copolymers and mixtures thereof.

6. The system according to claim 2, wherein the peptide with a net positive charge is selected from the group consisting of nuclear signaling peptides, mitochondrial signaling peptides, cell surface recognition peptides comprising the arginine-glycine-aspartic acid sequence and cell penetrating peptides.

7. The system according to claim 1, wherein the biologically active molecule is selected from the group consisting of DNA, mRNA, iRNA, microRNA, oligonucleotides and antisense sequence.

8. The system to claim 1, wherein said polysaccharide forms a complex together with the biologically active molecule, said complex being adsorbed on the surface of the nanoparticles.

9. The system according to claim 1, wherein the biologically active molecule is a DNA plasmid.

10. A pharmaceutical or cosmetic composition comprising the nanoparticle system as defined in claim 1.

* * * * *